United States Patent [19]

Tabak

[11] Patent Number: 4,547,612

[45] Date of Patent: Oct. 15, 1985

[54] PRODUCTION OF LUBRICANT AND/OR HEAVY DISTILLATE RANGE HYDROCARBONS BY LIGHT OLEFIN UPGRADING

[75] Inventor: Samuel A. Tabak, Wenonah, N.J.

[73] Assignee: Mobil Oil Corporation, New York, N.Y.

[21] Appl. No.: 654,348

[22] Filed: Sep. 25, 1984

[51] Int. Cl.$^4$ .................................................. C07C 3/20
[52] U.S. Cl. ................................. 585/533; 585/315; 585/316; 585/329; 585/415
[58] Field of Search ............... 585/315, 316, 329, 415, 585/533, 7 SM

[56] References Cited

U.S. PATENT DOCUMENTS

| | | | |
|---|---|---|---|
| 4,433,185 | 2/1984 | Tabak | 585/315 |
| 4,444,988 | 4/1984 | Capsuto et al. | 585/415 |
| 4,450,311 | 5/1984 | Wright et al. | 585/415 |
| 4,456,779 | 6/1984 | Owen et al. | 585/415 |
| 4,456,781 | 6/1984 | Marsh et al. | 585/415 |

*Primary Examiner*—D. E. Gantz
*Assistant Examiner*—A. Pal

[57] ABSTRACT

In a continuous process for upgrading lower olefin feedstock to higher hydrocarbons including the steps of combining olefinic feedstock with a pressurized liquid diluent stream comprising $C_5^+$ olefins, contacting the diluted feedstock with a shape selective medium pore acid zeolite catalyst under reaction conditions at elevated temperature in a pressurized reactor zone to convert olefins and recover reactor effluent at reaction conditions; an improvement has been found which comprises:

heating and separating reactor effluent in a primary phase separation zone to vaporize light and middle distillate hydrocarbon components into a first vapor phase stream and recover a heavy liquid stream from the primary separation zone, said heavy liquid stream containing at least 50% of those $C_{20}^+$ hydrocarbons recovered in the reactor effluent;

condensing a portion of the first vapor phase stream by cooling and recovering the dominant portion of a liquid olefinic recycle stream for combining with the feedstock, said recycle stream comprising a major portion of $C_6$ to $C_{18}$ hydrocarbons recovered in the reactor effluent; and further fractionating the heavy liquid stream from the primary separation zone to obtain a major lubricant product stream consisting essentially of substantially linear $C_{20}^+$ aliphatic hydrocarbons.

12 Claims, 5 Drawing Figures

4,547,612

PRODUCTION OF LUBRICANT AND/OR HEAVY DISTILLATE RANGE HYDROCARBONS BY LIGHT OLEFIN UPGRADING

FIELD OF THE INVENTION

This invention relates to a continuous technique for the manufacture of heavy distillate and lubricant range hydrocarbons. In particular, it provides a system for operating an olefins conversion plant wherein a oligomerization catalyst, such as shape selective medium pore crystalline zeolite of the ZSM-5 type, is employed for upgrading olefinic feedstocks containing $C_3^+$ alkenes at elevated temperature and pressure.

BACKGROUND OF THE INVENTION

Recent work in the field of olefin upgrading has resulted in a catalytic process for converting lower olefins to heavier hydrocarbons. Particular interest is shown in a technique developed by Garwood, et al., as disclosed in European patent application No. 83301391.5, published Sept. 29, 1983, incorporated herein by reference. Heavy distillate and lubricant range hydrocarbons can be synthesized over ZSM-5 type catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992 Garwood and Lee disclose the operating conditions for the Mobil Olefin to Gasoline/Distillate (MOGD) process for selective conversion of $C_3^+$ olefins to mainly aliphatic hydrocarbons. In a related manner, U.S Pat. Nos. 4,150,062 and 4,211,640 (Garwood et al) disclose a process for converting olefins to gasoline components.

In the process for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}^+$ aliphatic product. Lower olefinic feedstocks containing $C_2-C_8$ alkenes may be converted; however, the distillate mode conditions do not convert a major fraction of ethylene.

It is a main object of this invention to provide a continuous processes devised for upgrading olefins to valuable lubricants and/or heavy distillate fuel product. A typical reactive feedstock consists essentially of $C_3-C_6$ mono-olefins, with varying amounts of nonreactive paraffins and the like being acceptable components.

SUMMARY OF THE INVENTION

A continuous process has been devised for converting a feedstock comprising lower olefins to form higher hydrocarbons, particularly lubricant and heavy distillate product. This process comprises the methods and means for:

contacting olefinic feedstock under oligomerization/polymerization conditions at moderate reaction temperature and high pressure favorable to formation of high molecular weight aliphatic hydrocarbons with a shape selective medium pore acidic crystalline silicate zeolite catalyst in a reaction zone maintained under low severity conditions to prevent excessive cracking; recovering oligomerized hydrocarbon effluent containing high boiling hydrocarbon product and lower boiling olefinic components; separating the high boiling product by partially fractionating the effluent in a continuous product fractionator including the step of heating a high boiling product liquid fraction at temperature substantially higher than the reaction temperature, thereby providing a vapor fraction rich in lower boiling olefinic components; recycling a stream comprising at least a portion of the lower boiling fraction for further reaction in the reaction zone; and recovering a high boiling product stream comprising a major amount of the high boiling liquid fraction.

This technique is particularly useful for producing $C_{20}^+$ heavy hydrocarbons comprising lubricant or heavy distillate range compounds having a substantially linear molecular conformation from lower olefins, such as $C_3$ to $C_6$ mono-olefins.

These and other objects and features of the invention will be understood from the following detailed description and drawings.

THE DRAWINGS

DESCRIPTION OF THE PREFERRED EMBODIMENTS

Figure 1:
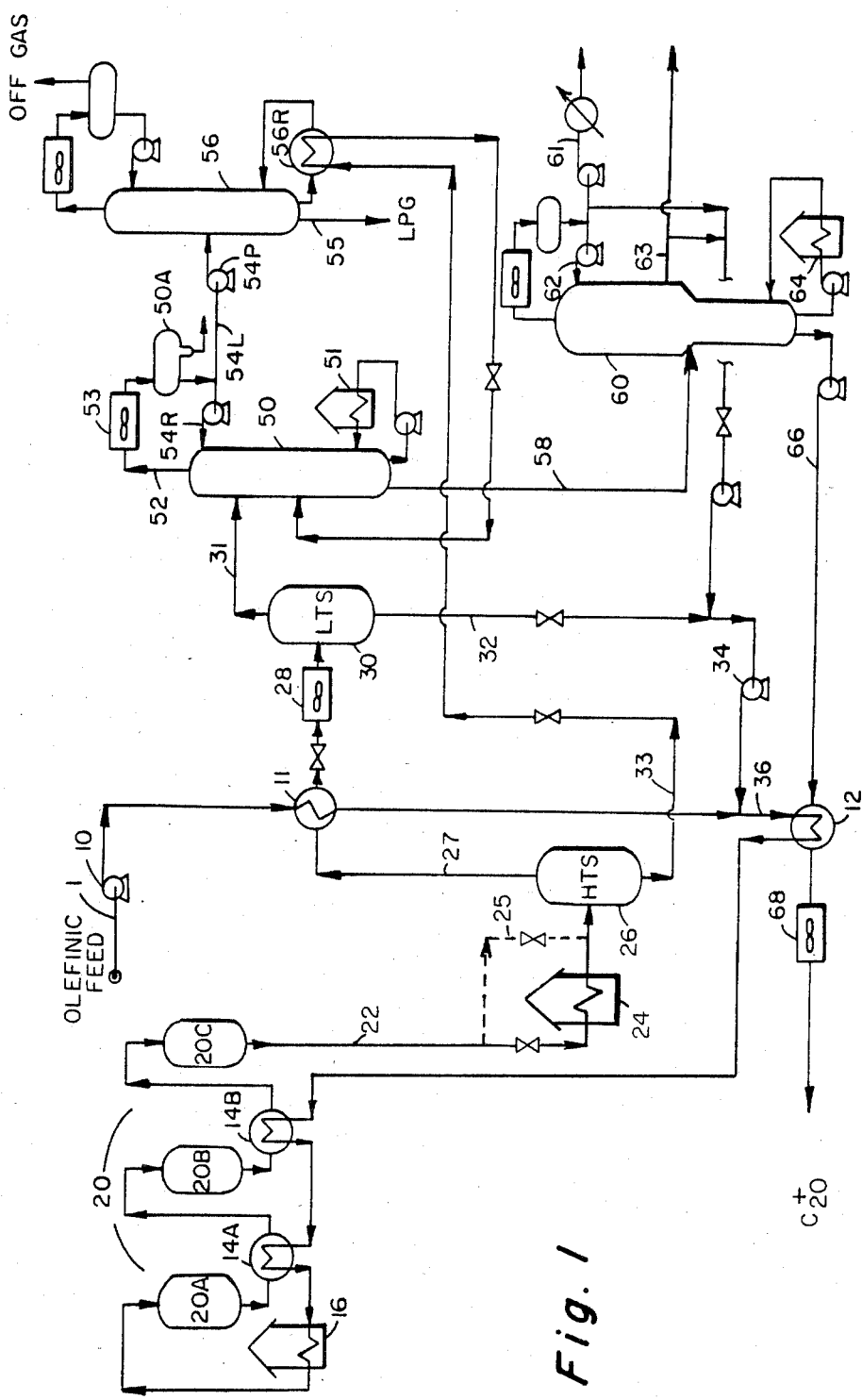
FIG. 1 is a schematic representation of a fixed bed reactor system and product separation system, according to the present invention, showing process flow streams and unit operations.

The oligomerization/polymerization catalysts preferred for use herein include the crystalline aluminosilicate zeolites having a silica to alumina molar ratio of at least 12, a constraint index of about 1 to 12 and acid cracking activity of about 160–200. Representative of the ZSM-5 type zeolites are ZSM5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable shape selective medium pore catalyst for fixed bed is a standard H-ZSM-5 zeolite (silica:alumina ratio = 70:1) with alumina binder in the form of cylindrical extrudates of about 1–5 mm. Unless otherwise stated in this description, the catalyst shall consist essentially of this standard ZSM5, which has an acid cracking value ($\alpha$-value) of about 160–200. Other pentasil catalysts which may be used in one or more reactor stages include a variety of medium pore ($\sim 5$ to $9A$) siliceous materials such as borosilicates, ferrosilicates, and/or aluminosilicates disclosed in U.S. Pat. Nos. 4,414,423, 4,417,086, 4,417,087 and 4,417,088, incorporated herein by reference.

Shape-selective oligomerization, as it applies to the conversion of $C_2$–$C_{10}$ olefins over ZSM5, is known to produce higher olefins up to $C_{30}$ and higher. As reported by Garwood in Intrazeolite Chemistry 23, (Amer. Chem. Soc., 1983), reaction conditions favoring higher molecular weight product are low temperature (200°–260° C.), high pressure (300 psig or greater) and long contact time (0.5–1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of ZSM-5 type catalysts impose shape-selective constraints on the configuration of the large molecules, accounting for the differences with other catalysts.

The following model reaction path for propylene is set forth for purposes of explanation, and it should be taken as a theoretical path, as the process is presently understood by workers in the field.

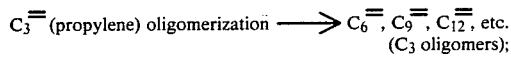
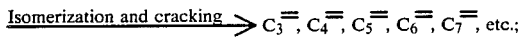
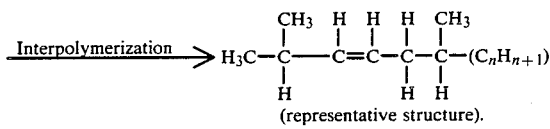

(representative structure).

The desired oligomerization-polymerization products are $C_{20}^+$ substantially linear aliphatic hydrocarbons. The ZSM-5 catalytic path for propylene feed provides a long chain with one methyl substituent per 4–5 carbon atoms in the straight chain. There are four distinct reactions occurring. First, propylene will oligomerize to distinct $C_6$, $C_9$, $C_{12}$, etc. oligomers. These then isomerize and recrack, forming a range of light olefins. These intermediates then repolymerize to an equilibrium (or pseudoequilibrium) distribution of heavier iso-olefin. As a result of having both forward (polymerization) and reverse (cracking), a continuous molecular weight distribution will occur in the product which can be independent of the carbon number of the starting olefin. For example, Garwood has previously shown, at constant temperature and pressure, virtually identical product distribution for feedstocks of ethylene ($C_2^=$) propylene ($C_3^=$), pentene ($C_5^=$), hexene ($C_6^=$), and decene ($C_{10}^=$). Structurally the final product is influenced by the pore structure of the catalyst For low carbon number products (i.e., $C_4$, $C_5$) isomer distribution is approximately at equilibrium. For the higher carbon numbers, the structure is primarily a methyl-branched straight olefinic chain with the maximum cross section of the chain limited by the 5.4×5.6 Angstrom dimension of the largest ZSM-5 pore. At conditions chosen to maximize heavy distillate range products ($C_{20}^+$) the raw aliphatic product is essentially mono-olefinic with 10% or less of the double bond in the alpha position. Overall branching is not extensive, with most branches being methyl at about one branch per four/five carbon atoms.

The flowsheet diagram of FIG. 1 shows the process relationships of the inventive process, depicting the conversion of the $C_3$–$C_6$ rich olefinic intermediate, multi-stage phase separation and recycle. Heavy hydrocarbons are recovered by fractionation and may be sent to a conventional hydrotreating unit for product finishing.

GENERAL PROCESS DESCRIPTION

The olefinic feedstock supply 1 is normally liquid and can be brought to process pressure by means of pump 10 and preheated by passing sequentially through a series of heat exchange means 11, 12 and reactant effluent exchangers 14B, 14A and furnace 16 prior to entering the catalytic reactor system 20.

A typical distillate mode first stage reactor system 20 is shown. A multi-reactor system is employed with inter-zone cooling, whereby the reaction exotherm can be carefully controlled to prevent excessive temperature above the normal moderate range of about 200° to 290° C. (400°–550° F.), especially in the final reaction zone. While process pressure may be maintained over a wide range, usually from about 2800 to over 20,000 kPa (400–3000 psia), the preferred pressure is about 7000 to 15,000 kPa (1000 to 2000 psia). The feedstock is heated to reaction temperature and carried sequentially through a series of zeolite beds 20A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.1 to 1, preferably about 0.5. The heat exchangers 14A and 14B provide inter-reactor cooling.

In a typical continuous process run under steady state conditions using a standard HZSM-5 catalyst, the average reactor temperature in the series of adiabatic fixed bed reactors is maintained below about 260° C. (500° F.). In order to optimize formation of high molecular weight $C_{20}^+$ hydrocarbons, effluent temperature from the terminal reactor 20C is kept substantially below about 290° C. (550° F.). Catalyst in the terminal position is preferably the most active in the series, being fresh or regenerated to maintain a high alpha value. By controlling the moderate reaction temperature, especially in the last bed, undesired cracking of the product $C_{20}^+$ hydrocarbons is minimized.

Unlike prior art "MOGD" processes, the reactor effluent is not cooled before fractionation. In order to obtain a relatively high boiling recycle, the effluent stream 22 may be further heated out of contact with the catalyst by furnace 24, preferably to a temperature at least about 30° C. (50° F.) higher than the maximum temperature attained by the exothermic reaction in the terminal reactor. A portion of the effluent may bypass the furnace via conduit 25, if desired, before entering the primary effluent separation unit 26. The effluent fractionation system has two main functions: (1) to provide primary means for separating suitable recycle materials and (2) to provide secondary means for recovering refined product streams of acceptable quality. The primary section is not required to provide streams of clearly defined boiling point components; and, therefore, phase separators in combination with flashing and heat exchange equipment can provide adequate recycle economically. However, the secondary fractionation function requires distinct separation according to molecular weight and boiling point, which usually dictates at least one distillation tower. While the embodiments disclosed herein include operatively connected separators, product splitters, debutanizers, etc., it is within the skill of the art to apply the inventive concept to a variety of effluent separation systems, to provide the required recycle and product streams for a continuous light olefin upgrading system according to the present invention.

The effluent mixture under process pressure and elevated temperature (e.g. 320° C.) enters a high temperature separator (HTS) 26, wherein high boiling product is recovered as a liquid rich in $C_{20}^+$ hydrocarbons; while vaporizing volatile components of the effluent stream, including the light and intermediate hydrocarbons, such as $C_1$ to $C_{19}$ aliphatics. Preferably the major portion (e.g. 50% to more than 90 wt %) of $C_{20}^+$ hydrocarbon components are contained in the high boiling liquid fraction. Overhead vapor is withdrawn through conduit 27, cooled indirectly by incoming feedstock in exchanger 11 and passed through air cooler 28 to condense a major amount of gasoline to middle distillate range hydrocarbons for recovery in the second phase separation unit 30. This condensed stream is withdrawn through conduit 32 to provide essentially all of the liquid olefinic recycle stream and pressurized by pump means 34 prior to combining with feedstock in conduit 36. Advantageously, the major portion of $C_6$ to $C_{18}$ hydrocarbon components are contained in the liquified recycle stream.

Liquid hydrocarbons rich in distillate are recovered from the primary separation zone 26 at process pressure, preferably about 1000 to 1500 kPa (150 to 220 psia) and passed via conduit 33 to debutanizer tower 50 for secondary fractionation at a lower stage therein where the heavy liquid contacts rising vapor from reboiler section 51 to vaporize dissolved lighter hydrocarbons, especially $C_4^-$ hydrocarbons present in the feedstock or generated during conversion. A vapor overhead stream from the second separation zone 30 is sent directly through conduit 31 to the debutanizer tower 50 at an intermediate stage. The debutanizer overhead stream 52 may be cooled by air cooler 53 to produce reflux 54 and recovered as LPG byproduct through conduit 55 from deethanizer 56.

The amount of recycle can be varied according to need. Light hydrocarbons and byproduct water are withdrawn from the debutanizer overhead accumulator 50A. The debutanizer bottoms stream 58, which is a heavier hydrocarbon stream containing gasoline and distillate range material, is sent to product splitter 60 where the heavier hydrocarbons are fractionated to provide a condensed gasoline product stream 61 and condensed reflux 62. A middle distillate (e.g. $C_{10}-C_{19}$) may be recovered at an intermediate point via conduit 63 for partial recycle if desired. Splitter tower 60 has a furnace fired reboiler section 64 which may be maintained at about 290° to 350° C. under low pressure (atmospheric or vacuum) to vaporize lower boiling components. If a significant fraction of the total $C_6$ to $C_{18}$ recycle components are taken from the secondary fractionator, the heat duty of primary furnace 24 can be decreased. Lubricant and heavy distillate products are recovered through conduit 66, and cooled by incoming feedstock in exchanger 12 and in cooler 68. Advantageously, the effluent liquid phase is fractionated to provide a major raw product stream consisting essentially of 290° C.+ aliphatic hydrocarbons comprising a major amount of $C_{20}^+$ aliphatic hydrocarbons. This raw olefinic product may then be hydrotreated in a separate process step (not shown) to provide a paraffinic lubricant and/or heavy distillate product. Details of a mild hydrogenation treatment may be obtained from U.S. Pat. No. 4,211,640, incorporated by reference, typically using Co or Ni with W/Mo and/or noble metals. The hydrotreated $C_{20}^+$ stream may be further fractionated to yield refined high grade lubricants of outstanding quality.

There are several advantages to the process design. The intermediate range hydrocarbon recycle consists essentially of $C_5^+$ hydrocarbons, with minor amounts of $C_4^-$ components. This recycle material preferably includes at least 50% of the $C_6$ to $C_{18}$ hydrocarbons from the reactor effluent. Having a relatively high heat capacity, it provides a good heat sink without diminishing feedstock olefin partial pressure and thereby maintaining a high olefin partial pressure at reactor inlet. The liquid recycle is economically repressurized by pumping, which requires modest power consumption. The debutanizer is operable at about 1000 kPa (150 psi) to condense all overhead without refrigeration, thus providing energy efficiency in obtaining the LPG byproduct.

Typical distillate/lubricant mode oligomerization operations are conducted over a fixed bed of HZSM5/alumina extrudate catalyst using the techniques described in U.S. Pat. No. 4,456,779 (Owen, et al.) and U.S. Pat. No. 4,433,185 (Tabak), incorporated herein by reference. Reactor sequencing and catalyst regeneration are known in the art.

Figure 2:
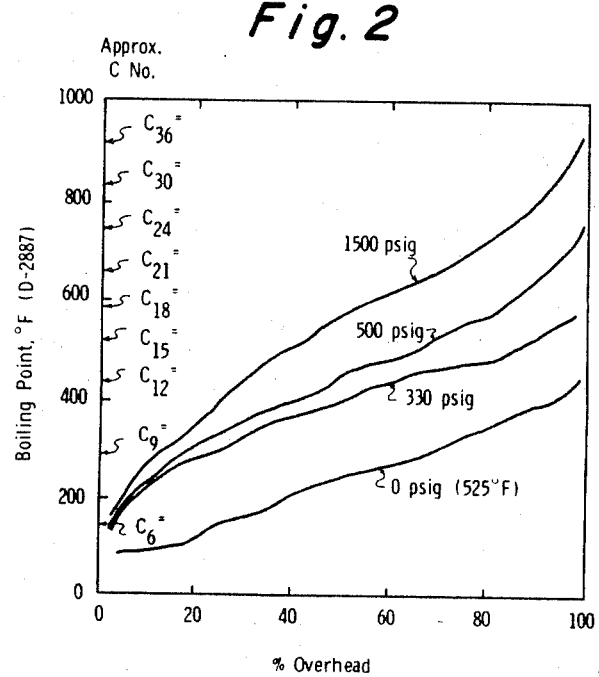
FIG. 2 is a graphic plot showing product distribution for a series of propylene conversion runs at various pressures.

In order to demonstrate the effect of pressure on the process, propylene is reacted at 204° C. and 0.4 WHSV over HZSM-5 in an isothermal reaction zone. FIG. 2 shows a correlation between boiling range of liquid product from 2400 to 10,400 kPa, with a low pressure run (274° C.) plotted for comparison. Propylene conversion is essentially complete at 204° C. under these conditions, and the liquid product includes all carbon numbers from $C_6$ to about $C_{36}$.

Figure 3:
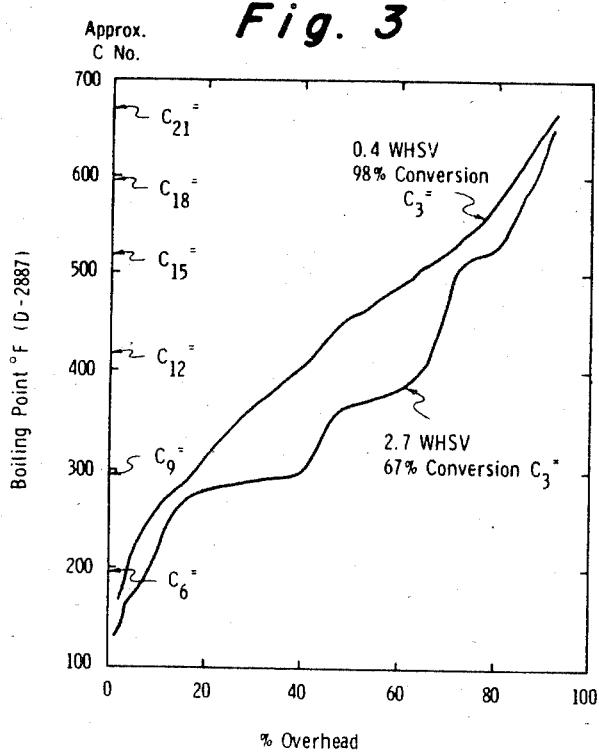
FIG. 3 is a graphic plot of propylene conversion over HZSM-5 at different space velocities.

In FIG. 3, the effect of contact time is depicted by comparing two runs using propylene feed at 204° C. and 3600 kPa. The liquid boiling plateaus in the higher space velocity run (2.7 WHSV) show evidence of oligomers, corresponding to the trimer, tetramer and pentamer of propylene formed at 67% conversion during short residence. This contrasts with the relatively smooth curve of a longer contact time (0.4 WHSV). The preferred operation with space velocity less than 1 provides essentially complete conversion of $C_3-C_{10}$ feedstock. It is a characteristic of the reaction path that the liquid product boiling point curve for propylene is substantially similar to that of a $C_{10}$ (1-decene) feed, at low space velocity (0.1 to 0.5), 232° F. reaction temperature and 10,500 kPa, for instance. This suggests that the two widely different charge olefins undergo a common intermediate stage.

Figure 4:
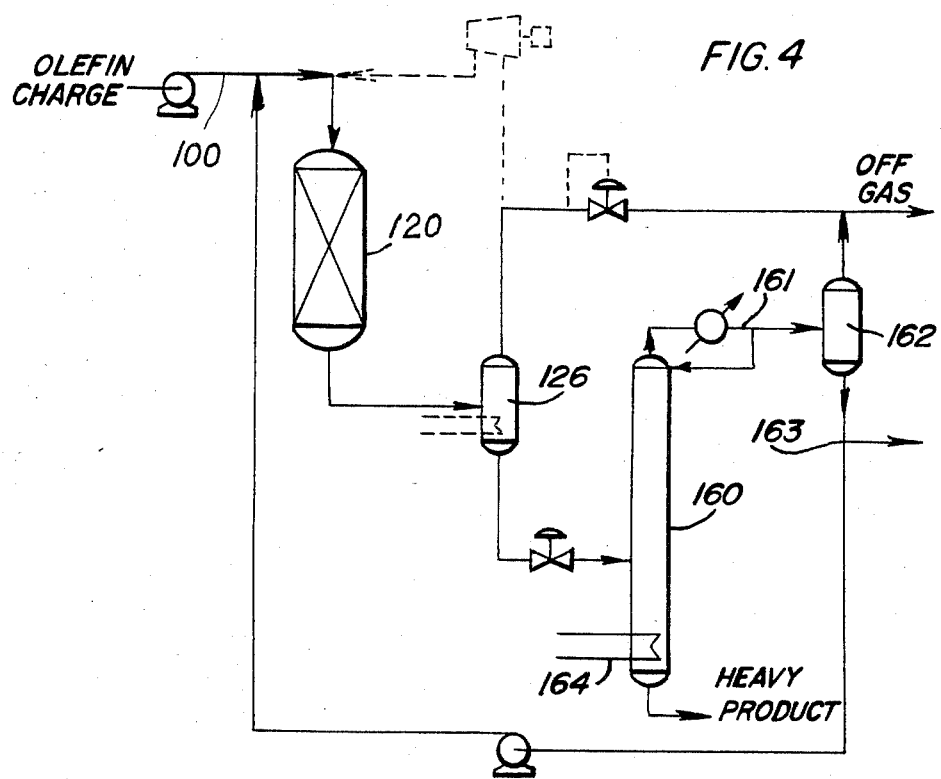
FIG. 4 is a schematic process diagram of an alternative embodiment of the invention.

An alternate embodiment of the inventive process is depicted in FIG. 4, which is a flow sheet for an olefins upgrading plant employing a fixed bed catalytic reactor. Simplified effluent fractionation and recycle streams are shown schematically, with reactor transfer and other details being omitted. Referring to FIG. 4, fresh olefinic feed 101 is pressurized, combined with recycle and heated to reaction temperature. This stream is passed over standard ZSM-5 catalyst in a continuous downflow vertical fixed bed reactor 120. In the following examples the average reactor temperature is maintained within he range of 205° to 260° C. (400° to 500° F.), at 1500 psig (10400 kPa) and a space velocity (WHSV based on feed olefin) of about 0.4 to 0.9. Under these conditions, a feedstock consisting of 10.7 weight percent propane, 27 wt % propylene, 26.2 wt % isobutane and 36.1 wt % butylene is converted. Reactor effluent is initially separated under process conditions in high temperature separator 126. Overhead vapor is passed through a back pressure regulator and recovered as off-gas. The liquid effluent stream is passed under fluid control to a continuous distillation tower 160 having a variable temperature reboiler to control still bottoms temperature substantially above the reactor temperature, thus providing a still overhead stream, which is cooled to condense a liquid recycle stream rich in $C_6$ to $C_{18}$ olefins from overhead receiver 162. Light hydrocarbons are recovered and combined with off-gas from phase separator 126. Data from a continuous run under varying process conditions are tabulated below:

selective medium pore acidic crystalline sillicate zeolite catalyst in a reaction zone maintained under low severity conditions to prevent excessive cracking;

recovering oligomerized hydrocarbon effluent containing high boiling hydrocarbon product and lower boiling olefinic components;

separating the high boiling product by partially fractionating the effluent in a continuous product fractionator including the step of heating a high boiling product liquid fraction at temperature substantially higher than the reaction temperature, thereby providing a vapor fraction rich in lower boiling olefinic components;

recycling a stream comprising at least a portion of the lower boiling fraction for further reaction in the reaction zone; said fraction containing the major

TABLE I

| | Days on Stream | | | | | | | | | |
|---|---|---|---|---|---|---|---|---|---|---|
| | 2 | 3 | 4 | 5 | 7 | 8 | 9 | 10 | 11 | 13 |
| Operating Conditions | | | | | | | | | | |
| Ave. Reactor Temp. °C. | 211 | 208 | 202 | 213 | 233 | 242 | 247 | 247 | 247 | 259 |
| Pressure, kPa | 10,400 | 10,400 | 10,400 | 10,400 | 10,400 | 10,400 | 10,400 | 10,400 | 10,400 | 10,400 |
| LHSV(Total) | 1.4 | 1.4 | 1.1 | 1.0 | 1.0 | 1.2 | 0.9 | 0.6 | 0.6 | 0.9 |
| LHSV(Olefin) | 0.9 | 0.9 | 0.7 | 0.7 | 0.6 | 0.8 | 0.6 | 0.4 | 0.4 | 0.6 |
| Gas Recycle (Mole/Mole Olefin) | — | — | — | — | — | — | — | — | — | — |
| Liq. Recycle (Vol/Vol Olefin) | 1.8 | 1.8 | 1.8 | 1.8 | 1.8 | 1.8 | 1.8 | 1.8 | 1.8 | 1.8 |
| Total Olefin Conv. Wt % | 99.18 | 98.61 | 97.74 | 98.09 | 99.08 | 98.86 | 98.93 | 98.74 | 97.81 | 98.44 |
| Propylene Conv., Wt % | 100.00 | 100.00 | 100.00 | 100.00 | 100.00 | 100.00 | 100.00 | 100.00 | 100.00 | 100.00 |
| Butylene Conv., Wt % | 98.43 | 97.06 | 94.84 | 96.00 | 98.44 | 97.84 | 97.55 | 97.12 | 94.99 | 96.42 |
| Product Yields (On Conv. Olfn.) | | | | | | | | | | |
| C1–C4 Saturates, Wt % | 3.20 | 4.58 | 6.54 | 6.57 | 8.35 | 9.36 | 11.71 | 13.16 | 31.40 | 10.45 |
| C5–330F Gasoline, Wt % | 18.17 | 13.87 | 16.07 | 12.23 | 11.50 | 9.06 | 8.48 | 8.54 | 10.47 | 12.69 |
| 330F–650F Distl., Wt % | 69.14 | 60.14 | 59.73 | 66.26 | 45.18 | 43.76 | 34.60 | 32.91 | 24.62 | 58.88 |
| 650F + Distl., Wt. % | 9.49 | 21.41 | 17.66 | 14.94 | 34.96 | 37.82 | 45.21 | 45.39 | 33.87 | 17.99 |
| Still Overhead, API | 47.7 | 48.9 | 42.3 | 49.2 | 409.2 | 38.8 | 37.2 | 39.4 | 39.9 | 39.6 |
| 5 Wt %, °C. | 109 | 101 | 102 | 101 | 112 | 111 | 113 | 113 | 101 | 112 |
| 50 Wt %, °C. | 216 | 218 | 230 | 217 | 239 | 243 | 247 | 244 | 218 | 222 |
| 95 Wt %, °C. | 314 | 300 | 318 | 291 | 322 | 328 | 337 | 334 | 312 | 298 |
| TOTAL LIQUID PRODUCT (Weighted average 50% boiling point °C.) | 237 | 264 | 261 | 263 | 294 | 301 | 322 | 320 | 332 | 278 |

Figure 5:
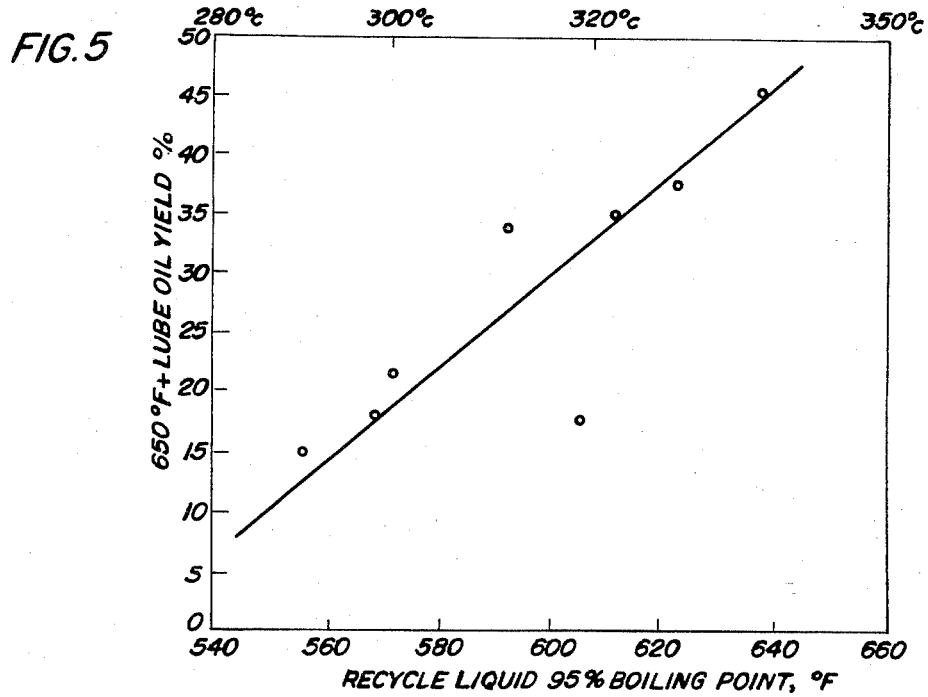
FIG. 5 is a graphic plot showing the effect of heavy product yield versus recycle boiling point.

These data clearly demonstrate that increasing the boiling point of recycled liquid provides a greater yield of high boiling (650° F.+) product. FIG. 5 is a graphic plot of the 95 wt % recycle liquid boiling point vs. high boiling still bottoms yield. The lube oil fraction of total process hydrocarbons increases dramatically from a very minor fraction to almost half of the total yield as the still bottoms temperature is increased to drive substantially all of the $C_6$ to $C_{18}$ hydrocarbons into the still overhead to provide a heavier condensed recycle liquid.

Various modifications can be made to the system, especially in the choice of equipment and non-critical processing steps. While the invention has been described by specific examples, there is no intent to limit the inventive concept as set forth in the following claims.

What is claimed is:

1. A continuous process for producing heavy hydrocarbons comprising lubricant or heavy distillate range compounds having a substantially linear molecular conformation from lower olefins, comprising:

contacting olefinic feedstock under oligomerization conditions at moderate reaction temperature and high pressure favorable to formation of high molecular weight aliphatic hydrocarbons with a shape portion of $C_6$ to $C_{18}$ hydrocarbon components;

recovering a high boiling product stream comprising at least 90 weight percent hydrocarbons boiling above 290° C.

2. The process of claim 1 wherein the catalyst comprises HZSM-5 and the oligomerization effluent is recovered at a temperature below about 290° C.

3. The process of claim 2 wherein the oligomerization is conducted at a pressure of at least 1000 kPa.

4. The process of claim 1 wherein the major portion of $C_{20}+$ hydrocarbon components are contained in the high boiling liquid fraction.

5. The process of claim 1 wherein the feedstock and recycle streams are combined under process pressure, heated to reaction temperature and passed through a multi-zone reactor system comprising a series of operatively connected fixed bed adiabatic catalytic reactors, with inter-reactor cooling to maintain the average reaction temperature in the reactor beds below about 260° C.

6. The process of claim 5 wherein the weight hourly space velocity is about 0.1 to 1, based on fresh feedstock olefins, and wherein the feedstock olefins consist essentially of $C_3$ to $C_6$ mono-olefins.

7. In the continuous process for upgrading lower olefin feedstock to higher hydrocarbons including the steps of combining olefinic feedstock with a pressurized liquid diluent stream comprising $C_5^+$ olefins, contacting the diluted feedstock with a shape selective medium pore acid zeolite catalyst under reaction conditions at elevated temperature in a pressurized reactor zone to convert olefins and recover reactor effluent at reaction conditions; the improvement which comprises:

heating and separating reactor effluent in a primary phase separation zone to vaporize light and middle distillate hydrocarbon components into a first vapor phase stream and recover a heavy liquid stream from the primary separation zone, said heavy liquid stream containing at least 50% of those $C_{20}^+$ hydrocarbons recovered in the reactor effluent;

condensing a portion of the first vapor phase stream by cooling and recovering the dominant portion of a liquid olefinic recycle stream for combining with the feedstock, said recycle stream comprising a major portion of $C_6$ to $C_{18}$ hydrocarbons recovered in the reactor effluent; and further fractionating the heavy liquid stream from the primary separation zone to obtain a major lubricant product stream consisting essentially of substantially linear $C_{20}^+$ aliphatic hydrocarbons.

8. The process of claim 7 wherein the catalyst comprises a silicate zeolite having a silica to alumina mole ratio of at least 12 to 1 and a constraint index of about 1 to 12.

9. The process of claim 8 wherein the catalyst comprises HZSM5, the feedstock olefin comprises a major amount of propylene and the lubricant product consists essentially of hydrocarbons having one methyl substituent per 4–5 carbon atoms.

10. The process of claim 7 wherein feedstock comprising a major amount of $C_3$–$C_6$ is combined with the olefinic recycle stream in a ratio of at least about 0.5 moles of recycle per mole of feedstock olefin and contacted with a fixed bed of acid aluminosilicate zeolite catalyst having a constraint index of about 1 to 12 at a reaction temperature of about 200° C. to 290° C. at process pressure of about 4000 to 21,000 kPa and at a weight hourly space velocity less than 1 to convert a major amount of feedstock olefin.

11. A process of claim 7 further comprising the step of hydrotreating said lubricant product stream.

12. The process of claim 7 wherein the effluent is heated under process pressure between the reactor zone and the primary separation zone to a temperature at least 30° C. higher than the effluent temperature leaving the reactor zone.

* * * * *